United States Patent [19]
Heilmann et al.

[11] Patent Number: 5,694,978
[45] Date of Patent: Dec. 9, 1997

[54] PROTECTIVE CAP ASSEMBLY FOR PROTECTING AND SEALING A TUBING

[75] Inventors: Klaus Heilmann, St. Wendel; Claus Jessen, Otzenhausen, both of Germany

[73] Assignee: Fresenius AG, Bad Homburg, Germany

[21] Appl. No.: 567,560

[22] Filed: Dec. 5, 1995

[30] Foreign Application Priority Data

Dec. 9, 1994 [DE] Germany .................. 94 19 630 U

[51] Int. Cl.$^6$ .................. F16L 55/10; B65D 41/04
[52] U.S. Cl. .................. 138/89; 138/103; 215/329
[58] Field of Search .................. 138/89, 90, 109, 138/103, 89.1–89.4; 215/329, 350, 333, 337–340, 356, 296; 220/228, 255, 256; 15/214

[56] References Cited

U.S. PATENT DOCUMENTS

| | | | |
|---|---|---|---|
| 3,557,989 | 1/1971 | Balda | 215/337 X |
| 3,595,419 | 7/1971 | Dukess | 215/329 |
| 3,612,320 | 10/1971 | Wassilieff | 214/329 X |
| 3,715,063 | 2/1973 | Susuki et al. | 215/329 X |
| 3,973,690 | 8/1976 | Schneider | 215/329 |
| 4,019,646 | 4/1977 | Imamura | 215/329 |
| 4,210,251 | 7/1980 | Grussen | 215/329 |
| 4,394,923 | 7/1983 | Sugyama | 215/329 |
| 4,597,758 | 7/1986 | Aalto et al. | 604/256 |
| 5,014,869 | 5/1991 | Hammond | 220/90.2 |
| 5,060,813 | 10/1991 | Gollasch et al. | 215/329 X |

FOREIGN PATENT DOCUMENTS

| | | |
|---|---|---|
| 350384 | 5/1928 | Belgium . |
| 527140 | 8/1939 | United Kingdom . |
| 83 03975 | 11/1983 | WIPO . |

*Primary Examiner*—Patrick Brinson
*Attorney, Agent, or Firm*—Henry M. Feiereisen

[57] ABSTRACT

A protective cap assembly for protecting and sealing a tubing used in the field of peritoneal dialysis, includes a plug that is closely fitted in one end of a tubing, and a protective cap which has first connection means for allowing a permanent attachment of the protective cap to the plug, and second connection means for allowing a detachable securement of the protective cap to the tubing.

13 Claims, 2 Drawing Sheets

5,694,978

PROTECTIVE CAP ASSEMBLY FOR PROTECTING AND SEALING A TUBING

BACKGROUND OF THE INVENTION

The present invention refers to a protective cap assembly for protecting and sealing a tubing of e.g. medical connectors for use in peritoneal dialysis. In particular, the present invention refers to a protective cap assembly of a type including a protective cap formed with connection means for attachment to a counterpiece, such as a closure member that is received in the tubing.

Peritoneal dialysis is a type of dialysis therapy that utilizes the membrane in a patient's peritoneal cavity for the purpose of separating waste products from the patient's fluid system. One type of peritoneal dialysis is referred to as continuous ambulatory peritoneal dialysis (CAPD) in which dialysis fluid is introduced from a solution bag into the patient's peritoneal cavity by a peritoneal catheter. After leaving the dialysis fluid in the peritoneal cavity for a certain period, spent fluid is drained from the peritoneal cavity to a drain bag and fresh fluid is infused from another solution bag.

Typical closure members are used to seal the connector or a coupling piece at the patient's peritoneal catheter when changing fluid bags or disconnecting the peritoneal catheter following dialysis. After replacing a fluid bag and sealing off the respective connector, the latter is secured by a protective cap which is screwed onto the connector.

If a further bag exchange should be performed, the protective cap must first be unscrewed before the closure member can be extracted. However, in particular the removal of the closure member is problematic because, on the one hand, germs can easily be transmitted to the connector and migrate into the peritoneal cavity of the patient, thereby possibly causing peritonitis, and, on the other hand, as the closure member sits closely fitted in the connector, a withdrawal thereof becomes difficult.

International publication WO 83/03975 discloses a protective cap, in particular for use in peritoneal dialysis procedures, which is lined with an absorbent material that is soaked with a disinfectant to maintain the connector end covered by the protective cap in a germfree environment. The use of such a protective cap harbors the same drawbacks as previously stated because the closure member can be extracted only separately from the protective cap.

SUMMARY OF THE INVENTION

It is an object of the present invention to provide a protective cap assembly for protecting and sealing a tubing, obviating the afore-stated drawbacks.

In particular, it is an object of the present invention to provide a protective cap assembly for protecting and sealing a tubing, which enables an extraction of a closure member at a same time the protective cap is removed from the tubing.

These objects and others which will become apparent hereinafter are attained in accordance with the present invention by forming the protective cap with first connection means that allows a permanent attachment of the protective cap to the counterpiece, such as a closure member, and with a second connection means that allows a detachable securement of the protective cap to the tubing.

As the first connection means accomplishes a permanent attachment of the protective cap with the closure member, a removal of the protective cap from the tubing automatically extracts the closure member from the tubing, without requiring the patient to touch the closure member. In addition, as the protective cap is detachably secured to the tubing by the second connection means, the protective cap is held in place, and an unintentional withdrawal of the closure member is prevented.

Through the protective cap assembly according to the present invention, the extra step of removing the closure member separately from the protective cap is eliminated so that the overall procedure becomes more comfortable for the patient, and there is no need for the patient to manually handle the closure member. Thus, a risk of contamination of the tubing is minimized.

Preferably, the first connection means is formed by at least one latching element, or by a threaded connection that is effective in only one direction, or by a saw-tooth rotating element such as a ratchet. These are only examples of possible connection means that provide a permanent attachment between two components.

When using a latching element to effect a permanent connection, the latching element is formed by at least one catch which is engageable in a groove of the counterpiece, or vice versa, i.e. the latching element is formed by at least one groove which is engageable by a catch formed on the counterpiece.

The detachable securement of the protective cap to the tubing may be effected for example by a threaded connection, a plug-in connection or a bayonet-type coupling. In all these configurations, the required force for removing the closure member can be kept small, e.g. through suitable configuration of the meshing thread profiles. Upon attachment of the protective cap onto the closure member, the latching element engages the closure member, e.g. a plug receivable in the tubing, to effect a permanent connection so that a removal of the protective cap is automatically followed by an extraction of the closure member from the tubing.

According to another feature of the present invention, the protective cap accommodates an absorbent material which retains an antiseptic that is released when applying pressure onto the absorbent material. Suitable examples for absorbent material include foamed polymer or a sponge or other porous material.

The present invention is also directed to a closure member that is used for sealing a tubing and is formed with connection means that cooperate with a protective cap according to the present invention to effect a permanent attachment between the closure member and the protective cap. Suitably, the connection means is provided in form of at least one latching element which cooperates with a complementary latching element of the protective cap.

The present invention is further concerned with a method of extracting a closure member from the tubing. Thus, in accordance with the present invention, the closure member is extracted by placing the protective cap over the closure member to effect a permanent connection therebetween while detachably securing the protective cap to the tubing, and by removing the protective cap from the tubing while the connection between the protective cap and the closure member is maintained.

A protective cap according to the present invention may be used in connection with an infusion tube, a catheter, or peritoneal catheter. Also the closure member may be attached to an infusion tube, a catheter, or a peritoneal catheter.

BRIEF DESCRIPTION OF THE DRAWING

The above and other objects, features and advantages of the present invention will now be described in more detail with reference to the accompanying drawing in which the sole

DETAILED DESCRIPTION OF A PREFERRED EMBODIMENT

Figure 1:
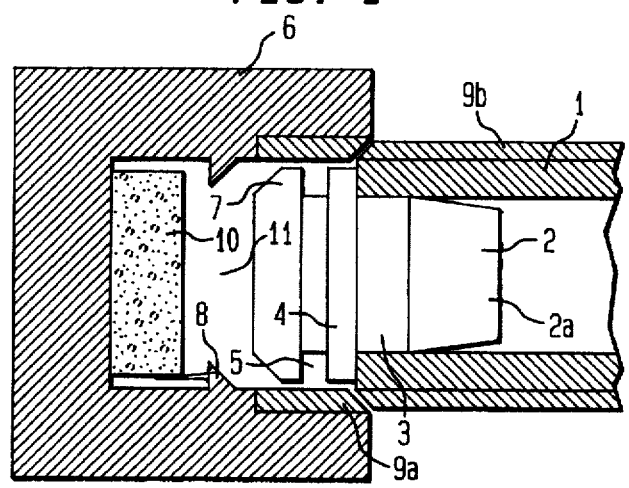
FIG. 1 shows a schematic, sectional view of a protective cap assembly, according to the present invention, for attachment to a tubing, with the protective cap not yet permanently attached to the closure member.

Turning now to FIG. 1, there is shown a schematic, sectional view of a protective cap assembly, according to the present invention, for attachment to a tubing 1, which e.g. may be a coupling piece or a connector used in peritoneal dialysis. In this context, reference is made to commonly assigned copending patent application by a different inventive entity, entitled "Apparatus for Controlling a Fluid Flow", filed simultaneously and based on unpublished German patent specification DE 44 43 714, the disclosure of which is incorporated herein by reference. However, it will be understood by persons skilled in the art that use of the protective cap assembly of this invention may also be suitable for use in other medical or technical applications and procedures which require a protection and sealing of tubes.

Received in the tubing 1 is a closure member which is configured in form of a profiled plug and generally designated by reference numeral 2. The plug 2 has a forward truncated cone shaped section 2a to facilitate insertion into the axial end of the tubing 1, a cylindrical section 3 which extends from the section 2a and fits closely in the tubing 1 to effect fluid-tight seal, and a head portion 4 which bears upon the axial end face of the tubing 1 and is spaced from a terminal piece 7 at formation of a circumferential groove 5.

Further shown in FIG. 1 is a protective cap of substantially C-shaped configuration, generally designated by reference numeral 6, which is detachably securable to the tubing 1. At its side facing the tubing 1, the protective cap 6 is provided with an internal thread 9a for threaded connection with an external thread 9b formed axially outside along the tubing 1. Axially behind the internal thread 9a of the protective cap 6 is a circular projection 8 to form a catch which is engageable in the groove 5 when screwing the protective cap 6 onto the tubing 1. The projection 8 has a cross section in form of a right triangle, with the hypotenuse facing a complementary equally slanted side of the terminal piece 7 to facilitate the attachment of the protective cap 6 to the plug 2.

Thus, when being screwed onto the tubing 1, the protective cap 6 moves in axial direction toward the plug 2 until the catch 8 moves past the end face 7 and is received in the groove 5. In this position, the catch 8 securely bears with its vertical side upon the opposing side of the terminal piece 7 to effect a permanent connection of the protective cap 6 with the plug 2. When unscrewing the protective cap 6 from the tubing 1, the plug 2 is automatically extracted from the tubing 1 by the protective cap 6, without requiring the patient to separately manipulate or touch the plug 2. It will be understood by persons skilled in the art that the protective cap 6 with the catch 8 and the plug 2 are made of suitably elastic material to enable a movement of the catch 8 past the terminal piece 7.

Figure 2:
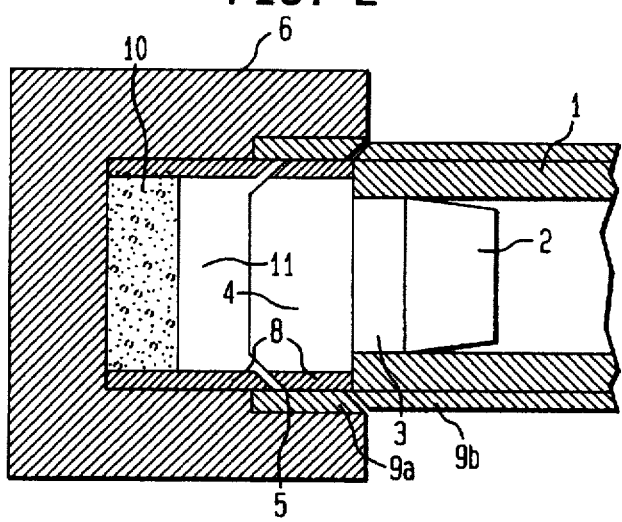
FIGS. 2 to 5 show schematic, sectional views of modified protective cap assemblies according to the present invention.
Figure 3:
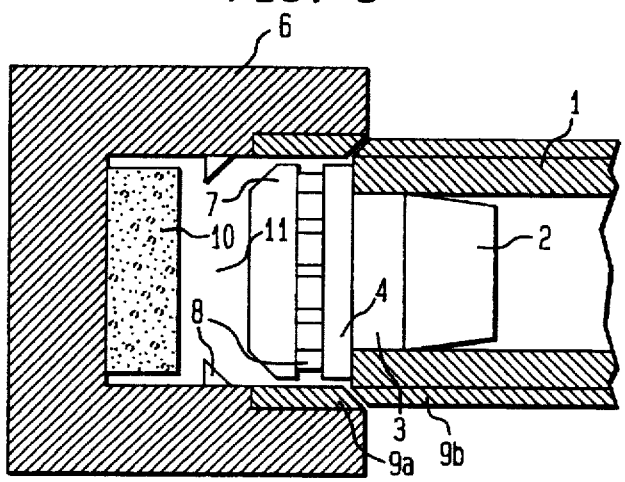
Figure 4:
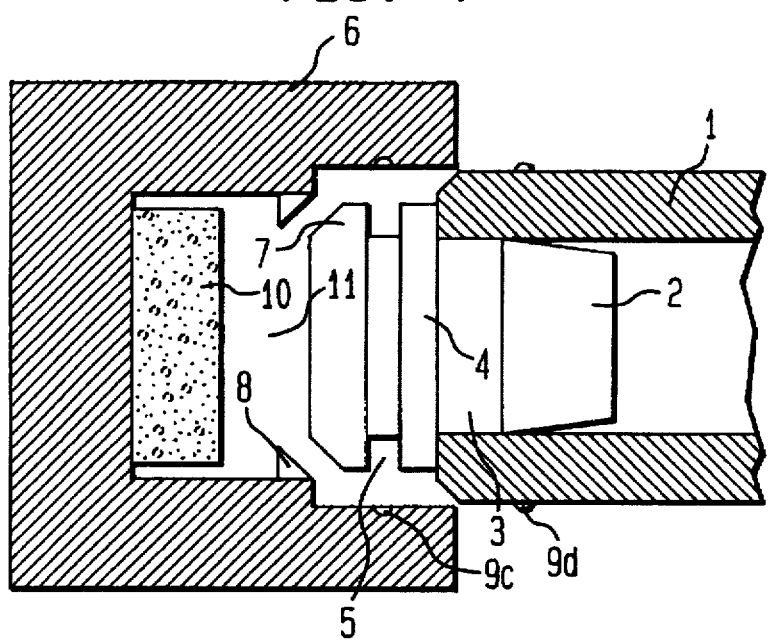
Figure 5:
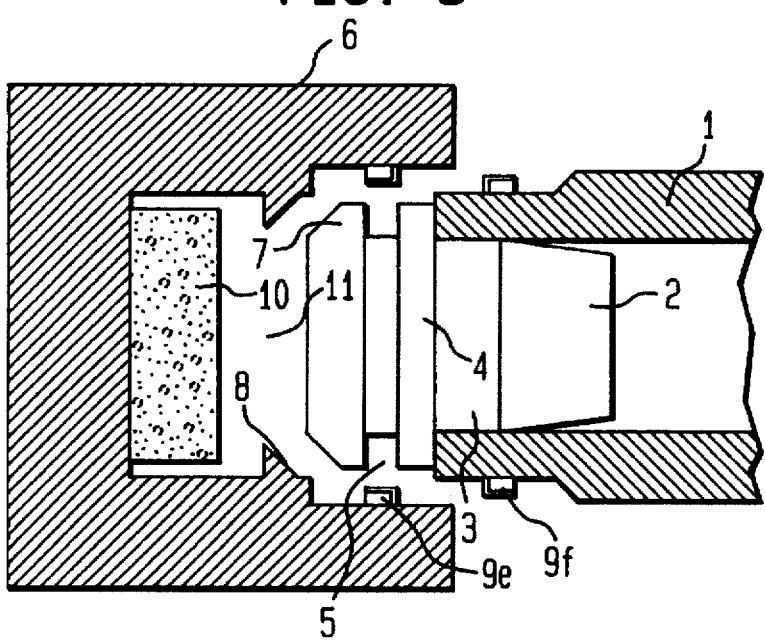

Persons skilled in the art will also understand that the connection between the protective cap 6 and the plug 2 via the projection 8 and groove 5 may be substituted by any other connection which enables a permanent attachment of the protective cap 6 to the plug 2. Examples of such connections include a threaded connection which is effective only in one direction, as shown in FIG. 2 or a serrated rotating element such as a ratchet, as shown in FIG. 3, or a plug-in connection with the protective cap 6 including a circumferential recess 9c about its inside wall surface for engagement by an annular protuberance 9d of the tubing 1, as shown in FIG. 4, or a bayonet-type coupling, as shown in FIG. 5, with grooves 9e in the protective cap 6 for engagement by pins 9f of the tubing 1. It is certainly also possible to provide the plug with a catch that engages a complementary groove in the protective cap.

As further shown in FIG. 1, the protective cap 6 exhibits an interior space 11 in which an antiseptic-retaining absorbent material 10 in form of a sponge or foamed polymer or other suitable porous material is disposed and attached to the inside wall in opposition to the plug 2. The absorbent material 10 releases the antiseptic when being subjected to pressure.

Thus, during attachment of the protective cap 6 onto the tubing 1, the end piece 7 of the plug 2 impacts on the absorbent material 10 to exert pressure thereon and to thereby cause a release of antiseptic. In this manner, the interior space 11 which may have been contaminated by airborne microorganisms is disinfected.

Other examples of such antiseptic-releasing discharge elements 10 include bubbles which are filled with antiseptic and burst during attachment of the protective cap 6 to the tubing 1. Antiseptics retained in the absorbent material 10 may include iodine/iodide or other suitable disinfectant such as e.g. "Citrosterile" on the basis of citric acid and marketed commercially by Fresenius AG, Germany, or "Lavasept" on the basis of biguanide. Other suitable disinfectants are peroxide compositions, ozone or hypochlorite which may also be produced in situ. Advantageously, the antiseptic is released into the interior space 11 only during attachment of the protective cap 6 onto the tubing 1, i.e. when the interior space 11 is sealed off.

At the conclusion of a bag exchange procedure during peritoneal dialysis, the plug 2 is initially forced into the tubing 1 by a suitable rotatable member of a type e.g. disclosed in the commonly owned copending patent application which has been previously referred to above, without requiring the patient to touch the plug 2 itself. Subsequently, the protective cap 6 is screwed onto to the tubing 1 via the meshing threads 9a, 9b, with the catch 8 being forced past the terminal piece 7 to engage the groove 5 and to effect the permanent connection between the protective cap 6 and the plug 2. During attachment of the protective cap 6, the plug 2 is ultimately forced against the absorbent material 10 so that antiseptic is released into the closed interior space 11. The interior space 11 is thus sterilized between two successive bag changes. When unscrewing the protective cap 6 during a following bag change, the plug 2 is extracted from the application in view of the profile of the meshing threads. There is no need to touch either the tubing 1 or the plug 2, thus contributing significantly to the safety of the peritoneal dialysis.

While the invention has been illustrated and described as embodied in a protective cap assembly for sealing off a tubing, it is not intended to be limited to the details shown since various modifications and structural changes may be made without departing in any way from the spirit of the present invention.

What is claimed as new and desired to be protected by Letters Patent is set forth in the appended claims:

1. A protective cap assembly for use in peritoneal dialysis for attachment to a plug received in one end of a peritoneal cavity connector which is in fluid communication with a patient's peritoneal cavity, said protective cap assembly comprising:
   - a protective cap defining an interior and including first connection means for allowing a permanent attachment of the protective cap to the plug, and second connection means for allowing a detachable securement of the protective cap to the peritoneal cavity connector; and
   - an antiseptic-releasing member secured interiorly of the protective cap for disinfecting the interior of the protective cap upon securement to the peritoneal cavity connector.

2. The protective cap assembly of claim 1 wherein the first connection means of the protective cap is formed by at least one latching element.

3. The protective cap assembly of claim 1 wherein the first connection means of the protective cap is formed by a threaded connection effective in only one direction.

4. The protective cap assembly of claim 1 wherein the first connection means of the protective cap is formed by a serrated rotating member.

5. The protective cap assembly of claim 2 wherein the latching element includes at least one projection for engagement in a groove of the plug.

6. The protective cap assembly of claim 2 wherein the latching element includes at least one groove for engagement by a projection of the plug.

7. The protective cap assembly of claim 1 wherein said second connection means is a threaded connection between the protective cap and the peritoneal cavity connector.

8. The protective cap assembly of claim 1 wherein said second connection means is a plug-in connection between the protective cap and the peritoneal cavity connector.

9. The protective cap assembly of claim 1 wherein said second connection means is a bayonet connection between the protective cap and the peritoneal cavity connector.

10. The protective cap assembly of claim 1 wherein the antiseptic-releasing member is an absorbent material soaked with antiseptic.

11. The protective cap assembly of claim 10 wherein the absorbent material is foamed polymer.

12. The protective cap assembly of claim 10 wherein the absorption material is a sponge.

13. In combination for use in peritoneal dialysis,
   - a plug received in one end of a peritoneal cavity connector in fluid communication with a patient's peritoneal cavity for securing the end in fluidtight manner;
   - a protective cap defining an interior and including first connection means for allowing a permanent attachment of the protective cap to the plug, and second connection means for allowing a detachable securement of the protective cap to the peritoneal cavity connector; and
   - an antiseptic-releasing member secured interiorly of the protective cap for disinfecting the interior of the protective cap upon securement to the peritoneal cavity connector.

* * * * *